US012440343B2

(12) United States Patent
Wills et al.

(10) Patent No.: US 12,440,343 B2
(45) Date of Patent: Oct. 14, 2025

(54) IMPLANT TRIAL HEAD

(71) Applicant: Encore Medical, L.P., Austin, TX (US)

(72) Inventors: Kevin Michael Wills, Austin, TX (US); Heather Fewell, Spring, TX (US)

(73) Assignee: Encore Medical, L.P., Austin, TX (US)

( * ) Notice: Subject to any disclaimer, the term of this patent is extended or adjusted under 35 U.S.C. 154(b) by 453 days.

(21) Appl. No.: 18/045,975

(22) Filed: Oct. 12, 2022

(65) Prior Publication Data

US 2023/0116976 A1 Apr. 20, 2023

Related U.S. Application Data

(60) Provisional application No. 63/262,675, filed on Oct. 18, 2021.

(51) Int. Cl.
*A61F 2/36* (2006.01)

(52) U.S. Cl.
CPC ........ *A61F 2/36* (2013.01); *A61F 2220/0025* (2013.01)

(58) Field of Classification Search
CPC ......... A61F 2/36; A61F 2/3609; A61F 2/4684
See application file for complete search history.

(56) References Cited

U.S. PATENT DOCUMENTS 5,188,402 A 2/1993 Colgate
7,179,296 B2 2/2007 Dooney
2004/0054421 A1 3/2004 McLean
2006/0173548 A1 8/2006 Auxepaules
2006/0206211 A1* 9/2006 Daniels .................... A61F 2/32 623/22.17
2015/0272740 A1 10/2015 Wakiyama et al.
2017/0000616 A1 1/2017 Grostefon

OTHER PUBLICATIONS

International Search Report and Written Opinion dated Mar. 31, 2023 in application No. PCT/US22/46539.
International Preliminary Report on Patentability dated Jun. 20, 2024 in application No. PCT/US22/46539.

* cited by examiner

*Primary Examiner* — Si Ming Ku
(74) *Attorney, Agent, or Firm* — Eversheds Sutherland (US) LLP

(57) ABSTRACT

An implant trial head includes a distal end, a proximal end including an opening in an exterior surface, and a cavity extending from the opening into the implant trial head. The cavity includes an asymmetric groove in an interior wall of the cavity, the groove aligned substantially perpendicular to a longitudinal axis of the implant trial head, and a cross-sectional diameter of the asymmetric groove. The implant trial head includes an O-ring positioned in the asymmetric groove.

17 Claims, 4 Drawing Sheets

IMPLANT TRIAL HEAD

TECHNICAL FIELD

This disclosure generally relates to temporarily coupling a trial component with a cavity to a component inserted into the cavity. More specifically, this disclosure relates to temporarily coupling a trial head to a femoral stem implant or trial component using an asymmetric groove and O-ring inside the trial head to mechanically couple the trial head to a taper portion of a femoral stem implant or a femoral stem trial component.

BACKGROUND

Many implant systems include one or more trial heads which will be used by a surgeon to do a 'fit check' before choosing the final implant. The trial heads can be used after the surgeon has implanted the final femoral stem component, meaning that the heads will have to be assembled with the precision taper on the femoral stem implants. During the "fit check" a number of trial heads maybe used. The trial head is placed on the precision taper and can be held on by friction so it does not come off accidently. However, the trial head also must be able to be easily removed without damaging the taper. Accordingly, it would be advantageous for a trial head to be configured to be both held on by friction so it does not come off accidently and be easily removed without damaging the taper.

SUMMARY OF THE INVENTION

The devices, systems, and methods of the present disclosure have several features, no single one of which is solely responsible for its desirable attributes. Without limiting the scope of this invention as expressed by the claims which follow, certain innovations will now be discussed briefly. After considering this discussion, and other section provided herein, one will understand how the features of embodiments of the asymmetric groove and O-ring structure of a trial head described in this disclosure provide several advantages.

One innovation includes an implant trial head, comprising an exterior surface, a distal end, and a proximal end, the trial head including an opening in the exterior surface, and a cavity in the implant trial head. The cavity extends from the opening into the implant trial head, and the cavity is configured to receive a taper portion of a femoral stem implant or a femoral stem trial component. The cavity comprises an interior surface defining several portions of the cavity. In some embodiments, the cavity comprises a first cavity portion having a distal end and a proximal end and a second cavity portion having a distal end and a proximal end, where the first and second cavity portion are configured to receive a component. The cavity includes a third cavity portion (also referred there as a "groove") formed in an interior wall of the cavity. The third cavity portion is asymmetric. The third cavity portion has a distal end, a proximal end, and a height defined between the proximal end and the distal end, the third cavity portion positioned between the first cavity and second cavity portions such that the proximal end of the third cavity portion is adjacent to the distal end of the first cavity portion, and the distal end of the third cavity portion is adjacent to the proximal end of the second cavity portion, and the third cavity portion tapering outward from the proximal end to the distal end such that a diameter of a cross-section of the third cavity portion increases from the proximal end to the distal end. The implant trial head further comprises an O-ring positioned laterally in the third cavity portion such that the O-ring circumferentially surrounds a central portion of the third cavity portion and contacts the interior surface in the third cavity portion. The asymmetry of the third cavity portion allows the O-ring to expand laterally outward farther when it is biased towards the distal end (for example, when a taper is inserted into the cavity) compared to when it is biased towards the proximal end (for example, when a taper in the cavity is moved towards the opening to remove the taper from the cavity).

The diameter of the O-ring can be less than a height of the third cavity portion (e.g., a height from the proximal end of the third cavity portion to the distal end of the third cavity portion) allowing movement of the O-ring between the proximal end of the third cavity and the distal end of the third cavity as the taper portion of a femoral stem is inserted into the trial head. That is, the height of the cavity in which the O-ring is positioned allows the movement of the O-ring within the third cavity portion in a direction along a longitudinal axis of the trial head. In some embodiments, the height of the third cavity portion from the proximal end to the distal end is between about 0.10 inches and about 0.20 inches. In some embodiments, the height of the third cavity portion from the proximal end to the distal end is between about 0.125 inches and about 0.165 inches. In some embodiments, the height of the third cavity portion from the proximal end to the distal end is about 0.145 inches, plus or minus 0.1 inches.

In some embodiments, the diameter of the O-ring is between about 0.05 inches and about 0.3 inches. In some embodiments, the diameter of the O-ring is between about 0.08 inches and about 0.13 inches. In some embodiments, the diameter of the O-ring is about 0.103 inches plus or minus 5%.

Embodiments of the trial head can include an asymmetric groove (or cavity) in which the O-ring is positioned. For example, in some embodiments, the interior surface of the third cavity portion includes a tapered wall having an angle of about 30 degrees, plus or minus 5 degrees, with respect to the longitudinal axis of the implant trial head, the tapered wall angling away from the longitudinal axis as it extends from the proximal end of the third cavity portion towards the distal end of the third cavity portion. In some embodiments, the interior surface of the third cavity portion includes a tapered wall having an angle of between about 5 degrees and 55 degrees with respect to the longitudinal axis of the implant trial head, the tapered wall angling away from the longitudinal axis as it extends from the proximal end of the third cavity portion towards the distal end of the third cavity portion. In some embodiments, the interior surface of the third cavity portion includes a tapered wall having an angle of between about 20 degrees and 40 degrees with respect to the longitudinal axis of the implant trial head, the tapered wall angling away from the longitudinal axis as it extends from the proximal end of the third cavity portion towards the distal end of the third cavity portion. In some embodiments, the interior surface of the third cavity portion includes a tapered wall having an angle with respect to the longitudinal axis of the implant trial head, the tapered wall angling away from the longitudinal axis as it extends from the proximal end of the third cavity portion towards the distal end of the third cavity portion allowing the O-ring to contact the tapered wall and move along the tapered wall from the proximal end of the third cavity portion towards the distal end of the third cavity portion when the tapered portion inserted into the implant trial head.

In some embodiments, the third cavity portion comprises a curved distal surface, and a curved proximal surface, wherein the tapered wall is positioned between the curved distal surface and the curved proximal surface. In some embodiments, the first cavity portion and the second cavity portion have a cross-sectional diameters that are aligned and sized to define a receiving portion of the cavity to receive the taper portion such that the taper portion can extend through the first, second, and third cavity portion, and the third cavity portion and the O-ring are sized such that the O-ring extends into the receiving portion the first distance when the O-ring is positioned in the proximal end of the third cavity portion and a second distance when the O-ring is positioned in the distal end of the third cavity portion, the first distance being greater than the second distance.

Another innovation includes an implant trial head, comprising a distal end, a proximal end including an opening in the exterior surface, and a cavity extending into the implant trial head from the opening, the cavity comprising an asymmetric groove aligned substantially perpendicular to a longitudinal axis extending from the proximal end to the distal end of the implant trial head. In some embodiments, the implant trial head further includes an O-ring positioned in the asymmetric groove. In some embodiments, the cavity further comprises a distal end, a proximal end, and a height defined between the proximal end and the distal end, and wherein the diameter of the O-ring is less than height of the third cavity. In some embodiments, the cavity further comprises a circumferential angled wall defining cross-sections of the cavity, the angled wall aligned such that a diameter of a cross-section of the cavity at the proximal end is less than the diameter of a cross-section of the cavity at the distal end.

BRIEF DESCRIPTION OF THE DRAWINGS

The features and advantages of the devices and methods described herein will become more fully apparent from the following description and appended claims, taken in conjunction with the accompanying drawings. These drawings depict only several embodiments in accordance with the disclosure and are not to be considered limiting of its scope. In the drawings, similar reference numbers or symbols typically identify similar components, unless context dictates otherwise. In some instances, the drawings may not be drawn to scale.

DETAILED DESCRIPTION OF CERTAIN INVENTIVE ASPECTS

The following detailed description is directed to certain specific embodiments of the invention. However, the invention can be embodied in a multitude of different ways. It should be apparent that the aspects herein may be embodied in a wide variety of forms and that any specific structure, function, or both being disclosed herein is merely representative of one or more embodiments of the invention. An aspect disclosed herein may be implemented independently of any other aspects and that two or more of these aspects may be combined in various ways. For example, various aspects and dimensions of an implant trial head coupling to a portion of a femoral stem component device are described herein, and are described in different ways, and any of these aspects and dimensions of the portions and structure (e.g., the size and shape of an asymmetric grove, the size of an O-ring) can be used in suitable combinations, and thus the invention may be practiced, using any number of the aspects set forth herein. In addition, disclosed devices may be implemented, or such a method may be practiced, using other structure, functionality, or structure and functionality in addition to, or other than one or more of the aspects set forth herein.

Overview of Technology

A trial head can be used by the surgeon to do a 'fit check' before choosing the final implant. The trial head can be used after the surgeon has implanted the final femoral stem component, so that the trial head will have to assemble with the precision taper on the femoral stem implant. The trial head may also be used before implanting the final femoral stem component as the surgeon may use the trial head on a trial femoral stem component.

One way of facilitating the temporary assembly of a trial head on the taper portion of a femoral stem component is to use a rubber O-ring within the trial head. When the taper portion is inserted into the trial head, the O-ring contacts the taper portion and creates some friction and the O-ring presses between an exterior surface of the taper portion that is inserted into the trial head and an interior cavity wall within the trial head in which the O-ring is positioned. This allows the trial head to easily be pressed onto the taper portion and grip the taper portion without requiring the taper portion to have any unique features. This also allows the trial head to be pulled off the taper portion without causing damage to the taper portion, and it does not require the exertion of undue force on the femoral stem component. It is desirable that the O-ring allows for the trial head to be very easily assembled onto the taper portion but still grip the taper portion well enough such that the trial head does not accidently come off while in the wound.

Figure 4:
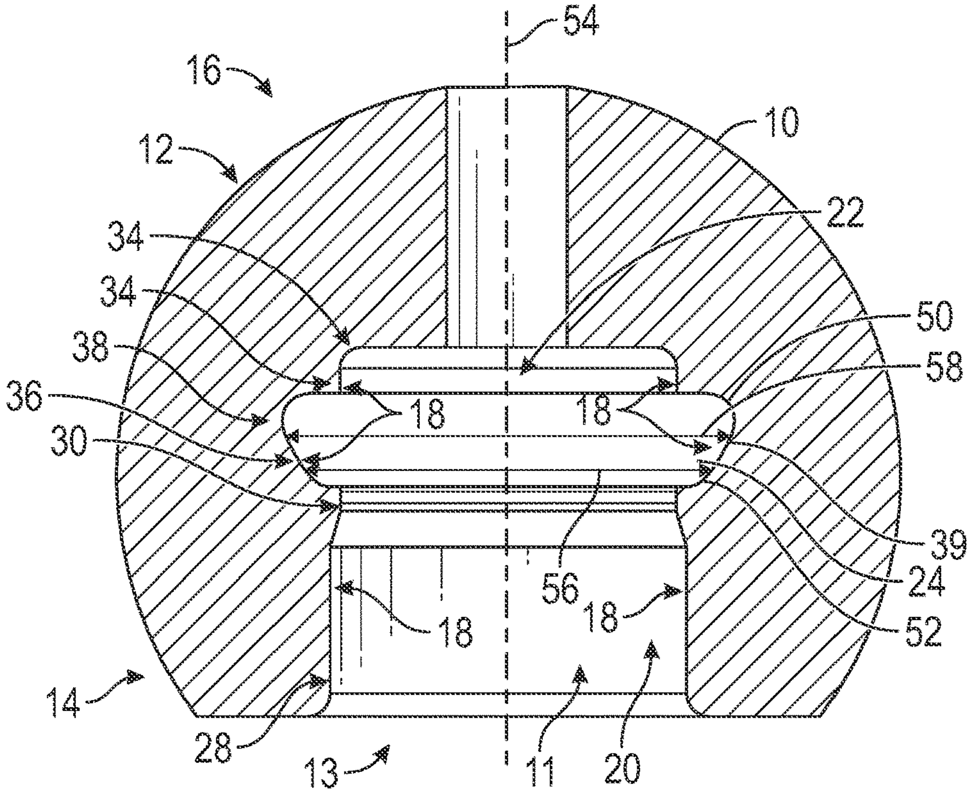
FIG. 4 illustrates a cross-sectional elevation view of an example of an implant trial head having a cavity with a first cavity portion, the second cavity portion, and the third cavity portion, the third cavity portion positioned between the first cavity portion and the second cavity portion, and where the third cavity portion has a cross-sectional diameter that increases as the third cavity portion extends from its proximal end to its distal end.
Figure 5:
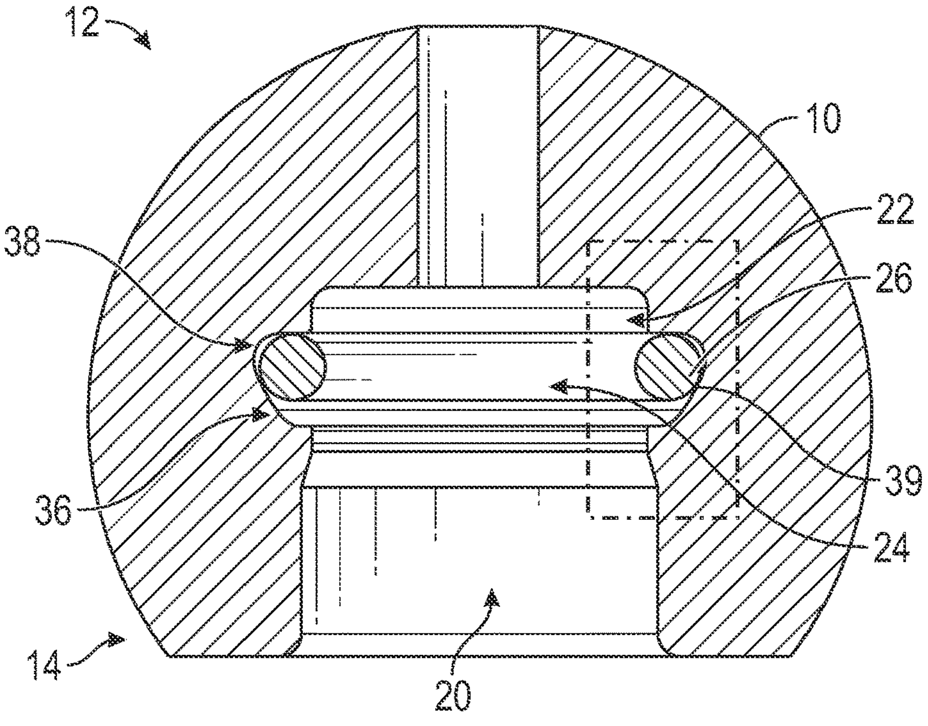
FIG. 5 illustrates a cross-sectional elevation view of the implant trial head of FIG. 4 including a cross-sectional view of an O-ring positioned in the third cavity portion.

To address this problem, embodiments of the invention described herein include a unique shape for the groove (or cavity) that the O-ring is positioned in. The groove can be non-symmetrical in its cross-section diameter (e.g., have a varying cross-sectional diameter) to achieve easy assembly when coupled to the taper portion and allowing its removal from the taper portion, while still achieving a tight fit on the taper portion. While the trial head is being pushed onto the taper portion, the O-ring is biased to (or moves to) a distal end (e.g., a top or upper portion) of the groove and outward by the taper portion, away from the center portion of the trial head. As illustrated in FIGS. 4 and 5, the shape at the top of the groove allows the O-ring to move outward without compressing the O-ring and thereby minimizes the effort needed to push the head onto the taper portion. When the trial head is pulled off or dislodges from the taper portion (accidently or otherwise), the O-ring is moved to a proximal portion (e.g., bottom or lower portion) of the groove where the shape of the groove wedges the O-ring tightly onto the taper portion, thereby pressing and gripping the trial head tightly on the taper portion. The shape, size, configuration of embodiments of a trial head having an asymmetric groove/cavity are further described below in reference to the figures.

Figure 1:
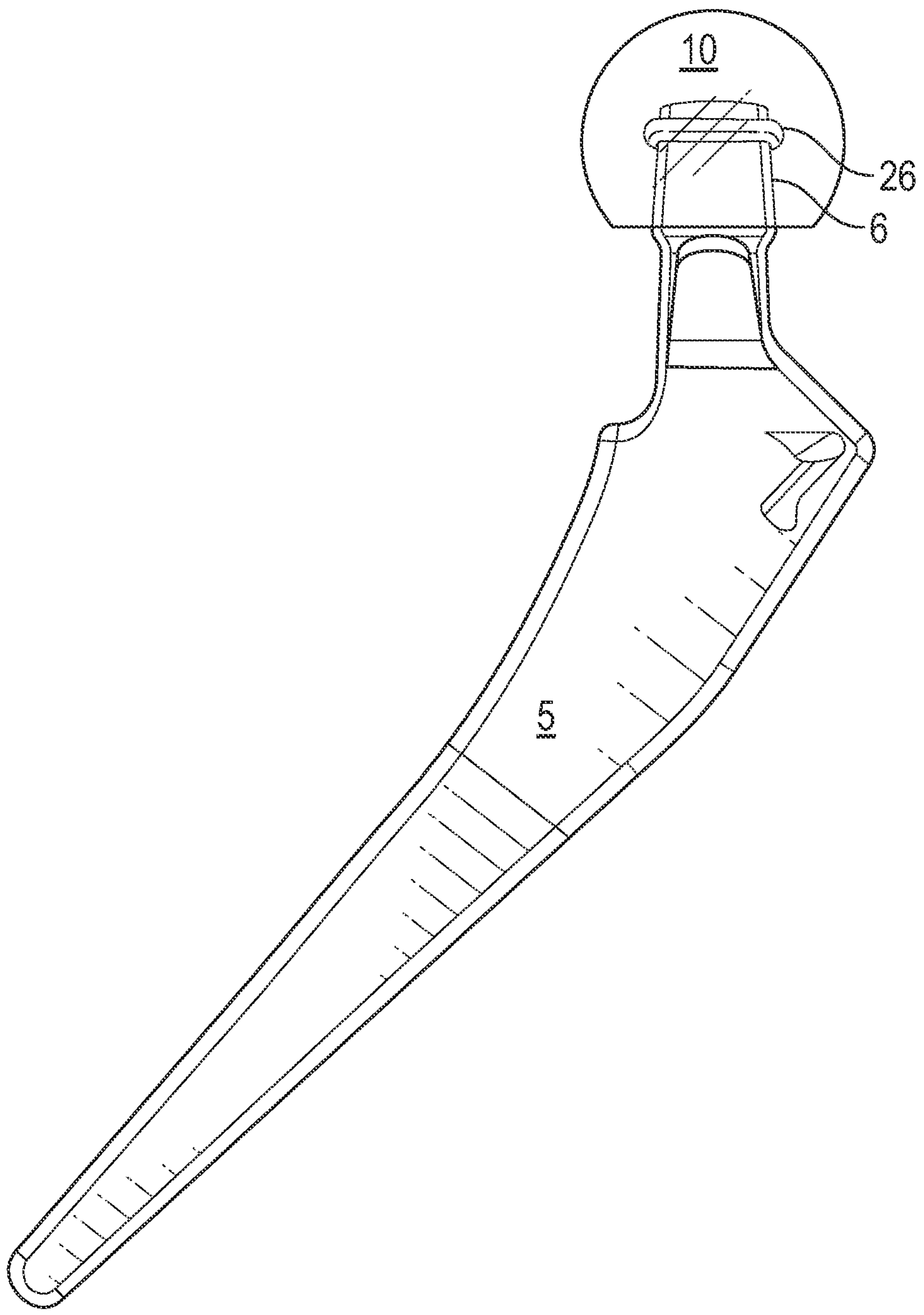
FIG. 1 illustrates an example of the implant trial head coupled to a taper portion of a femoral stem component.

The following is a list of certain annotations and components that are described and enumerated in this disclosure in reference to the above-listed figures. However, any aspect, structure, feature, or operational function of the devices illustrated in the figures, whether or not named out separately herein, can form a portion of various embodiments of the invention and may provide basis for one or more claim limitation relating to such aspects, with or without additional description. The annotations and enumerated components include:

5 femoral stem component
6 taper portion of the femoral stem component
10 trial head
11 cavity
12 exterior surface trial head
13 opening
14 proximal end of trial head
16 distal end of trial head
18 surface of cavity 11 (interior surface)
20 first cavity portion
22 second cavity portion
24 third cavity portion
26 O-ring
28 proximal end first cavity portion
30 distal end first cavity portion
32 proximal end second cavity portion
34 distal end second cavity portion
36 proximal end third cavity portion
38 distal end third cavity portion
39 tapered wall of third cavity portion
40 angle A
42 diameter D of O-ring
44 height H of third cavity portion (from proximal end to distal end)
46 distance between un-biased O-ring and interior surface of third cavity portion at distal end
48 distance O-ring extends inward into third cavity portion past the area where the taper portion of the femoral stem component is received in the third cavity
50 curved distal surface of third cavity portion
52 curved proximal surface of third cavity portion
54 longitudinal axis
56 cross-sectional diameter of third cavity near proximal end
58 cross-sectional diameter of third cavity near distal end Illustrative Examples of Device for Assembling Implant Systems Turning now to the figures, FIG. 1 illustrates an example of an implant trial head 10 coupled to a taper portion 6 of a femoral stem component 5. As can be seen through the trial head 10 (shown to be translucent in this figure), the trial head includes an O-ring 26 positioned laterally within the trial head 10 such that when the taper portion 6 is inserted into the trial head 10, the taper portion 6 passes through the center of the O-ring 26, and the O-ring 26 couples the trial head 10 to the taper portion 6 by a frictional force between the surface of the O-ring 26 and the taper portion 6.

Figure 2:
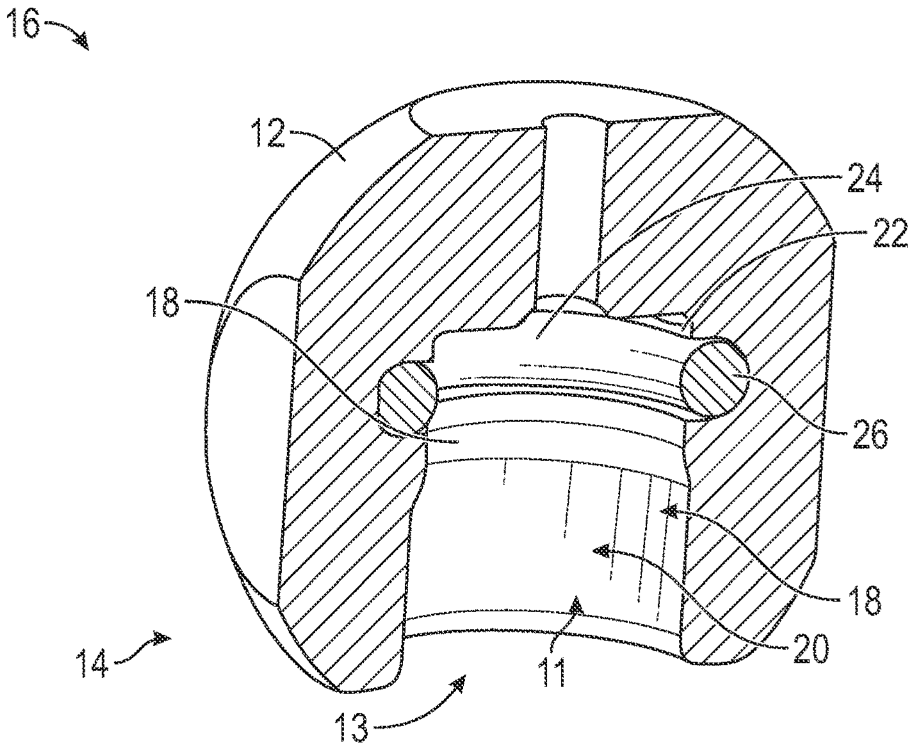
FIG. 2 is a perspective cross-sectional view of an example of an implant trial head that includes an O-ring for coupling the implant trial head to a taper portion of a femoral stem component.

FIG. 2 is a perspective cross-sectional view of an example of an implant trial head that includes an O-ring 26 for coupling the implant trial head 10 to a taper portion 6 of a femoral stem 5. As illustrated in FIG. 2, the trial head 10 includes a proximal end 14, a distal end 16, an opening 13, and a cavity 11 extending from the opening 13 into the trial head. The cavity 11 includes a surface 18. The illustrated cavity 11 may include a first cavity portion 20, a second cavity portion 22, and a third cavity portion 24, each defined by a portion of surface 18. The O-ring 26 is positioned within the third cavity portion 24. In this embodiment, the third cavity portion 24 includes a symmetrical wall (e.g., either flat or curved) such that the O-ring 26 is held in-place and cannot move (or substantially move) from one side of the cavity to the other, and the friction force between the O-ring 26 and a taper portion in the cavity 11 is relatively constant when the taper portion is inserted or removed.

Figure 3:
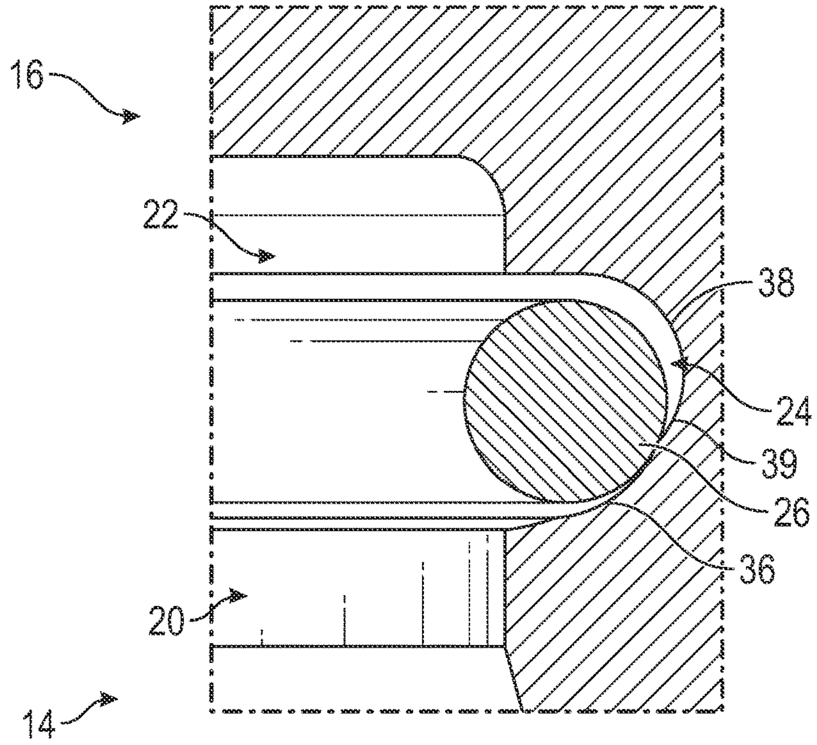
FIG. 3 is a cross-sectional zoomed view (portion from FIG. 5 illustrated by the dashed-dotted line in FIG. 5) of an asymmetric cavity (or groove) in an implant trial head, the asymmetric cavity including an angle surface which allows movement of the O-ring in the lateral direction as the O-ring moves from a proximal portion of the cavity to a distal portion of the cavity, for example, when a taper portion of a femoral stem component is coupled to the implant trial head.

FIG. 3 is a cross-sectional zoomed view of an asymmetric cavity (third cavity portion) 24 in an implant trial head. The asymmetric cavity 24 is sometimes referred to herein as a "groove." The figure is a zoomed portion of FIG. 5, as indicated by the dashed-dotted box in FIG. 5. A dimension across the asymmetric cavity 24 (e.g., that is perpendicular to the longitudinal axis 54) is longer on the distal end 38 of the asymmetric cavity 24 than the proximal end 38 of the asymmetric cavity 24. The asymmetric cavity 24 includes an angled surface 39 which allows more movement of the O-ring 26 in the lateral direction as the O-ring 26 moves from a proximal end 36 of the third cavity portion 24 towards a distal end 38 of the third cavity portion 24 for example, when a taper portion of a femoral stem component is inserted into and coupled to the implant trial head. The third cavity portion 24 in which the O-ring 26 is positioned is further described in FIGS. 4-6 below.

FIG. 4 illustrates a cross-sectional elevation view of an example of an implant trial head 10 having an exterior surface 12, an opening 13 in the exterior surface 12 at the proximal end 14 of the trial head 10. The trial head 10 includes a cavity 11 extending into the trial head from the opening 13. Cavity 11 is defined by an interior surface 18. The cavity 11 includes a first cavity portion 20, a second cavity portion 22, and the third cavity portion 24, the third cavity portion 24 positioned between the first cavity portion 20 and the second cavity portion 22, and where the third cavity portion 24 has a cross-sectional diameter that increases as the third cavity portion 24 extends from its proximal end 36 towards its distal end 38. The first cavity portion 20 includes a proximal end 28 and a distal end 30. The second cavity portion 22 includes a proximal end 32 and a distal end 34. The third cavity portion 24 includes a proximal end 36 and a distal end 38. The third cavity portion 24 includes tapered (or angled) wall 39 that laterally extends away from the longitudinal axis 54 of the trial head 10 as the tapered wall extends from proximal end 36 to the distal end 38. The third cavity portion 24 also includes a curved distal surface 50 on the distal end 38 of the third cavity portion 24, in a curved proximal surface 52 on the proximal end 36 of the third cavity portion 24. FIG. 4 also illustrates a cross-sectional diameter 56 of the third cavity portion 24 near the proximal end 36 of the third cavity portion 24, and a cross-sectional diameter 58 of the third cavity portion 24 near the distal end 38 of the third cavity portion 24. Because of the tapered wall 39 angling outward as it extends from the proximal end 36 of the third cavity portion 24 towards the distal end 38 of the third cavity portion 24, the length of the cross-sectional diameter 56 is less than the length of the cross-sectional diameter 58.

FIG. 5 illustrates a cross-sectional elevation view of the implant trial head 10 of FIG. 4. FIG. 5 also includes a cross-sectional view of an O-ring 26 positioned in the third cavity portion 24. In this figure, the O-ring 26 is positioned at the distal end 38 of the third cavity portion 24, which would be the position of the O-ring 26 when a taper portion is inserted into the cavity 11 and contacts the O-ring 26 and extends through the O-ring 26 moving the O-ring 26 towards the proximal end 38 of the third cavity portion 24. The dashed box indicates a portion of the figure that is enlarged for detail in FIG. 3.

In use, when a taper portion of a femoral stem component 6 is inserted into the opening 13 and through the cavity 11, the taper portion extends through third cavity portion 24 and the O-ring 26, such that the O-ring 26 is circumferentially positioned around a section of the taper portion and provides a frictional fit. As the taper portion is inserted through the first cavity portion 20, through the third cavity portion 24, and into the second cavity portion 22, the O-ring 26 moves from the proximal end 36 of the third cavity portion 24 to the distal end 38 of the third cavity portion 24. The tapered wall 39 structure allows the O-ring 26 to expand slightly such that the taper portion can be easily inserted. When the taper portion is moved the opposite direction, out of the cavity 11, the O-ring 26 moves from the distal end 38 to the proximal end 36 of the third cavity portion 24, and the tapered wall 39 structure constricts the O-ring 26 and provides a tighter frictional fit between the O-ring 26 and the taper portion.

Figure 6:
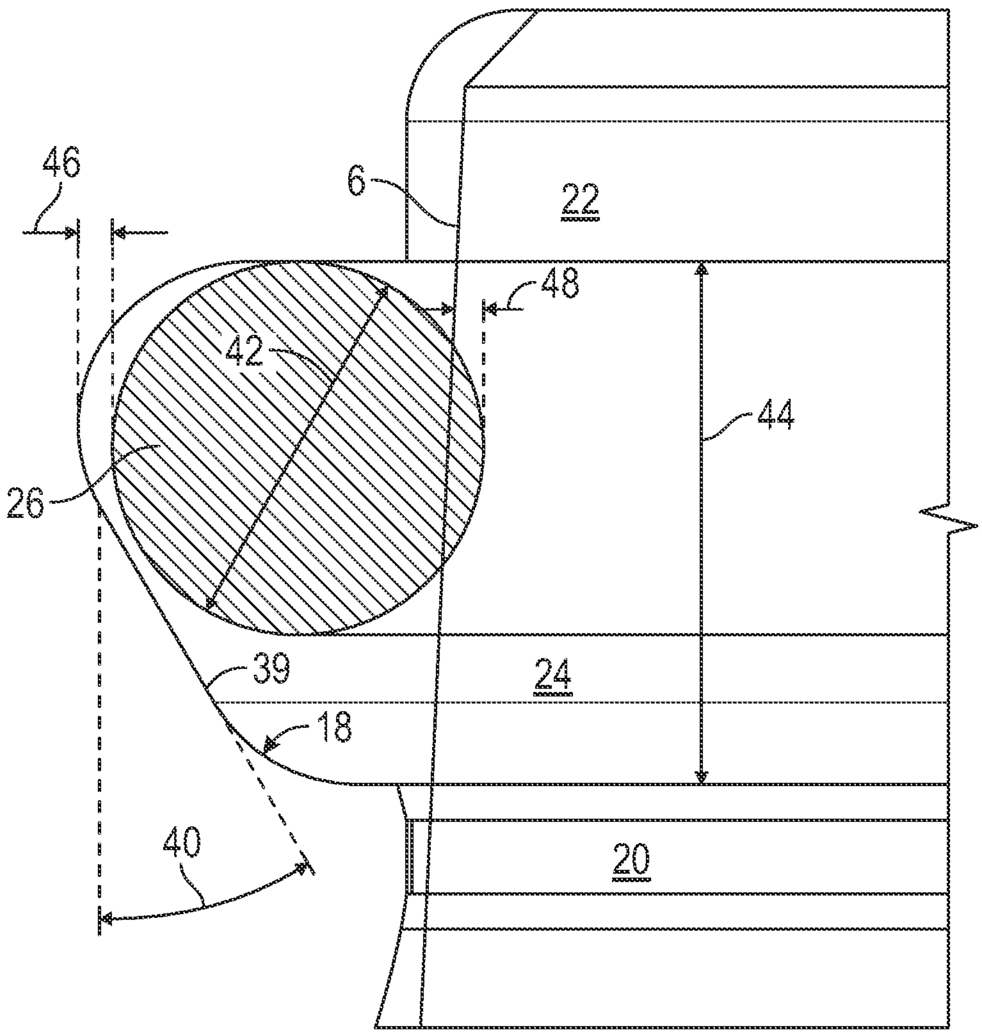
FIG. 6 illustrates various dimensions of an example of the third cavity portion of the implant trial head illustrated in FIGS. 3 and 4.

FIG. 6 illustrates various dimensions of an example of the third cavity portion 24 of the implant trial head 10 illustrated in FIGS. 3 and 4. Various embodiments can have different sizes of an O-ring 26, a different angle of a tapered wall 39, and a different height of H 44 of the third cavity portion 24 as described in examples below.

For example, in some embodiments, the O-ring 26 has a diameter D 42 of approximately 0.103 inches. In some embodiments, the O-ring 26 has a diameter D 42 of 0.103 inches plus or minus about 5% (e.g., plus or minus 0.005 inches). In some embodiments, the O-ring 26 has a diameter D 42 of 0.103 inches plus or minus about 10% (e.g., plus or minus 0.01 inches). In some embodiments, the O-ring 26 has a diameter D 42 of 0.103 inches plus or minus about 20% (e.g., plus or minus 0.02 inches). In various embodiments, the O-ring 26 has a diameter between about 0.05 inches and 0.30 inches. In various embodiments, the O-ring 26 may have a diameter between about 0.08 inches and 0.13 inches. In some embodiments, the O-ring 26 has a diameter of any of, or between any two of the following diameter dimensions: 0.05 inches, 0.06 inches, 0.07 inches, 0.08 inches, 0.09 inches, 0.10 inches, 0.11 inches, 0.12 inches, 0.13 inches, 0.14 inches, 0.15 inches, 0.16 inches, 0.17 inches, 0.18 inches, 0.19 inches, 0.20 inches, 0.21 inches, 0.22 inches, 0.23 inches, 0.24 inches, 0.25 inches, 0.26 inches, 0.27 inches, 0.28 inches, 0.29 inches, and 0.30 inches. In some embodiments, preferably the O-ring 26 has a diameter of between about 0.05 inches and 0.2 inches. However, in various embodiments, the O-ring 26 may have other diameters less than 0.05 inches, or greater than 0.30 inches, that are suitable to provide a frictional fit.

For example, in some embodiments, tapered wall 39 tapers at an angle A 40 of about 30° relative to the longitudinal axis 54 of the trial head 10, as illustrated in FIG. 6. The angle of the tapered wall 39 may vary based on particular embodiments. In some embodiments, the tapered wall 39 tapers at an angle A of between about 1° and about 60° relative to the longitudinal axis 54 of the trial head 10. In some embodiments, the tapered wall 39 tapers at an angle A of between about 20° and about 40° relative to the longitudinal axis 54 of the trial head 10. For example, the angle A of the tapered wall can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 degrees, plus or minus 0.5 degrees.

For example, in some embodiments, height H 44 of the third cavity portion 24 can be about 0.145 inches. However, the height H of the third cavity portion 24 can vary based on the particular embodiment. In some embodiments, the height H 44 of the third cavity portion 24 is between about 0.06 inches and about 0.21 inches. In some embodiments, the height H 44 of the third cavity portion 24 is between about 0.125 inches and about 0.165 inches. In various embodiments, the H 44 of the third cavity portion 24 is at, or between two of the following height dimensions: 0.03 inches, 0.04 inches, 0.05 inches, 0.06 inches, 0.07 inches, 0.08 inches, 0.09 inches, 0.10 inches, 0.11 inches, 0.12 inches, 0.13 inches, 0.14 inches, 0.15 inches, 0.16 inches, 0.17 inches, 0.18 inches, 0.19 inches, 0.20 inches, 0.21 inches, 0.22 inches, 0.23 inches, 0.24 inches, 0.25 inches, 0.26 inches, 0.27 inches, 0.28 inches, 0.29 inches, and 0.30 inches. In other embodiments, but not typically, a height dimension of the third cavity may be greater than 0.30 inches.

As illustrated in FIG. 6, due to the shape and size of the third cavity portion 24 and the diameter of the O-ring 26, the distance 46 between the outside edge of the O-ring 26 and the surface of the third cavity portion 24 can be about 0.001 inches to about 0.250 inches according to some embodiments. Also, the shape and size of the third cavity portion 24 and the diameter of the O-ring 26 are configured such that a portion of the O-ring extends into part of the third cavity portion 24 that receives the taper portion 6 by a small distance 48 (FIG. 6) to provide a frictional fit, for example, about 0.010 inches. The asymmetric shape of the third cavity 24 allows the O-ring 26 to expand outward when the taper is inserted into the cavity and contacts the O-ring 26. The examples of dimensions and angles described herein are suitable for many embodiments, however, such dimensions and angles may vary based on the particular application or embodiment.

IMPLEMENTATION CONSIDERATIONS

The foregoing description details certain embodiments of the systems, devices, and methods disclosed herein. It will be appreciated, however, that no matter how detailed the foregoing appears in text, the systems, devices, and methods can be practiced in many ways. As is also stated above, it should be noted that the use of particular terminology when describing certain features or aspects of the invention should not be taken to imply that the terminology is being re-defined herein to be restricted to including any specific characteristics of the features or aspects of the technology with which that terminology is associated.

Conditional language such as, among others, "can," "could," "might" or "may," unless specifically stated otherwise, are otherwise understood within the context as used in general to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Headings are included herein for reference and to aid in locating various sections. These headings are not intended to limit the scope of the concepts described with respect thereto. Such concepts may have applicability throughout the entire specification.

Many variations and modifications may be made to the above-described embodiments, the elements of which are to be understood as being among other acceptable examples. All such modifications and variations are intended to be included herein within the scope of this disclosure. The foregoing description details certain embodiments. It will be appreciated, however, that no matter how detailed the foregoing appears in text, the systems and methods can be practiced in many ways. As is also stated above, it should be noted that the use of particular terminology when describing certain features or aspects of the systems and methods should not be taken to imply that the terminology is being re-defined herein to be restricted to including any specific characteristics of the features or aspects of the systems and methods with which that terminology is associated.

It will also be understood that, when a feature or element (for example, a structural feature or element) is referred to as being "connected", "attached" or "coupled" to another feature or element, it may be directly connected, attached, or coupled to the other feature or element or intervening features or elements may be present. In contrast, when a feature or element is referred to as being "directly connected", "directly attached" or "directly coupled" to another feature or element, there may be no intervening features or elements present. Although described or shown with respect to one embodiment, the features and elements so described or shown may apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments and implementations only and is not intended to be limiting. For example, as used herein, the singular forms "a", "an" and "the" may be intended to include the plural forms as well, unless the context clearly indicates otherwise. It will be further understood that the terms "comprises" and/or "comprising," when used in this specification, specify the presence of stated features, steps, operations, processes, functions, elements, and/or components, but do not preclude the presence or addition of one or more other features, steps, operations, processes, functions, elements, components, and/or groups thereof. As used herein, the term "and/or" includes any and all combinations of one or more of the associated listed items and may be abbreviated as "/".

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

Spatially relative terms, such as "forward", "rearward", "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features due to the inverted state. Thus, the term "under" may encompass both an orientation of over and under, depending on the point of reference or orientation. The device may be otherwise oriented (rotated 90 degrees or at other orientations) and the spatially relative descriptors used herein interpreted accordingly. Similarly, the terms "upwardly", "downwardly", "vertical", "horizontal" and the like may be used herein for the purpose of explanation only unless specifically indicated otherwise.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise.

For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, may represent endpoints or starting points, and ranges for any combination of the data points. For example, if a particular data point "10"

and a particular data point "15" may be disclosed, it is understood that greater than, greater than or equal to, less than, less than or equal to, and equal to 10 and 15 may be considered disclosed as well as between 10 and 15. It is also understood that each unit between two particular units may be also disclosed. For example, if 10 and 15 may be disclosed, then 11, 12, 13, and 14 may be also disclosed.

Although various illustrative embodiments have been disclosed, any of a number of changes may be made to various embodiments without departing from the teachings herein. For example, the order in which various described method steps are performed may be changed or reconfigured in different or alternative embodiments, and in other embodiments one or more method steps may be skipped altogether. Optional or desirable features of various device and system embodiments may be included in some embodiments and not in others. Therefore, the foregoing description is provided primarily for the purpose of example and should not be interpreted to limit the scope of the claims and specific embodiments or particular details or features disclosed.

The examples and illustrations included herein show, by way of illustration and not of limitation, specific embodiments in which the disclosed subject matter may be practiced. As mentioned, other embodiments may be utilized and derived therefrom, such that structural and logical substitutions and changes may be made without departing from the scope of this disclosure. Such embodiments of the disclosed subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve an intended, practical or disclosed purpose, whether explicitly stated or implied, may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The disclosed subject matter has been provided here with reference to one or more features or embodiments. Those skilled in the art will recognize and appreciate that, despite of the detailed nature of the example embodiments provided here, changes and modifications may be applied to said embodiments without limiting or departing from the generally intended scope. These and various other adaptations and combinations of the embodiments provided here are within the scope of the disclosed subject matter as defined by the disclosed elements and features and their full set of equivalents.

What is claimed is:

1. An implant trial head, comprising:

an exterior surface;

a distal end;

a proximal end including an opening in the exterior surface;

a cavity in the implant trial head and configured to receive a taper portion of a femoral stem component, the cavity extending from the opening into the implant trial head, the cavity comprising an interior surface defining portions of the cavity including:

a first cavity portion having a distal end and a proximal end;

a second cavity portion having a distal end and a proximal end, the first cavity portion and second cavity portion configured to receive the taper portion of the femoral stem component;

a third cavity portion having a distal end, a proximal end, and a height defined between the proximal end and the distal end, the third cavity portion positioned between the first and second cavity portions such that the proximal end of the third cavity portion is adjacent to the distal end of the first cavity portion, and the distal end of the third cavity portion is adjacent to the proximal end of the second cavity portion, and the third cavity portion tapering outward from the proximal end to the distal end such that a diameter of a cross-section of the third cavity portion increases from the proximal end to the distal end; and an O-ring positioned laterally in the third cavity portion such that the O-ring contacts the interior surface in the third cavity portion, a diameter of the O-ring being less than the height of the third cavity portion allowing movement of the O-ring between the proximal end of the third cavity and the distal end of the third cavity as the taper portion the femoral stem component is inserted into the trial head.

2. The implant trial head of claim 1, wherein the height of the third cavity portion from the proximal end to the distal end is between about 0.01 inches and about 0.3 inches.

3. The implant trial head of claim 1, wherein the height of the third cavity portion from the proximal end to the distal end is between about 0.125 inches and about 0.165 inches.

4. The implant trial head of claim 1, wherein the height of the third cavity portion from the proximal end to the distal end is about 0.145 inches, plus or minus 0.1 inches.

5. The implant trial head of claim 1, wherein the diameter of the O-ring is between about 0.05 inches and about 0.3 inches.

6. The implant trial head of claim 1, wherein the diameter of the O-ring is between about 0.08 inches and about 0.13 inches.

7. The implant trial head of claim 1, wherein the diameter of the O-ring is about 0.103 inches plus or minus 5%.

8. The implant trial head of claim 1, wherein the interior surface of the third cavity portion includes a tapered wall having an angle of about 30 degrees, plus or minus 5 degrees, with respect to a longitudinal axis of the implant trial head, the tapered wall angling away from the longitudinal axis as it extends from the proximal end of the third cavity portion towards the distal end of the third cavity portion.

9. The implant trial head of claim 1, wherein the interior surface of the third cavity portion includes a tapered wall having an angle of between about 1 degrees and 60 degrees with respect to the longitudinal axis of the implant trial head, the tapered wall angling away from the longitudinal axis as it extends from the proximal end of the third cavity portion towards the distal end of the third cavity portion.

10. The implant trial head of claim 1, wherein the interior surface of the third cavity portion includes a tapered wall having an angle of between about 20 degrees and 40 degrees with respect to the longitudinal axis of the implant trial head, the tapered wall angling away from the longitudinal axis as it extends from the proximal end of the third cavity portion towards the distal end of the third cavity portion.

11. The implant trial head of claim 1, wherein the interior surface of the third cavity portion includes a tapered wall having an angle with respect to the longitudinal axis of the implant trial head, the tapered wall angling away from the longitudinal axis as it extends from the proximal end of the third cavity portion towards the distal end of the third cavity portion allowing the O-ring to contact the tapered wall and move along the tapered wall from the proximal end of the third cavity portion towards the distal end of the third cavity portion when the tapered portion inserted into the implant trial head.

12. The implant trial head of claim 11, wherein the third cavity portion comprises a curved distal surface on the distal end of the third cavity portion, and a curved proximal surface on the proximal end of the third cavity portion, wherein the tapered wall is positioned between the curved distal surface and the curved proximal surface.

13. The implant trial head of claim 1, wherein the first cavity portion and the second cavity portion have cross-sectional diameters that are aligned and sized to define a receiving portion of the cavity to receive the taper portion of a femoral stem component such that the taper portion can extend through the first, second, and third cavity portion, and the third cavity portion and the O-ring are sized such that the O-ring can expand outward at the distal end of the third cavity farther than it can expand outward at the proximal end of the third cavity portion.

14. An implant trial head, comprising:

an exterior surface;

a distal end;

a proximal end including an opening in the exterior surface; and a cavity extending into the implant trial head from the opening, the cavity comprising an asymmetric groove aligned substantially perpendicular to a longitudinal axis extending from the proximal end to the distal end of the implant trial head, wherein the cavity extending into the implant trial head from the opening is further comprised of a first cavity portion, a second cavity portion, and a third cavity portion positioned between the first cavity portion and the second cavity portion, and wherein the third cavity portion further comprises a distal end, a proximal end, and a height defined between the proximal end and the distal end, and wherein a diameter of an O-ring is less than height of the third cavity portion.

15. The implant trial head of claim 14, wherein the asymmetric groove is positioned within the third cavity portion.

16. The implant trial head of claim 14, wherein the cavity further comprises a circumferential angled wall defining a diameter of cross-sections of at least a portion of the cavity, the cross-sections aligned perpendicular to a longitudinal axis of the cavity.

17. The implant trial head of claim 16, wherein the angled wall is aligned such that a diameter of a cross-section of the asymmetric groove of the cavity at the proximal end is less than a diameter of a cross-section of the asymmetric groove of the cavity at the distal end.

* * * * *